(12) United States Patent
Brown

(10) Patent No.: US 10,940,045 B2
(45) Date of Patent: Mar. 9, 2021

(54) WASHABLE THERMOPLASTIC ELASTOMER FOAM AND ARTICLES INCORPORATING SAME

(71) Applicant: Brown Innovation, LLC, Lake Quivira, KS (US)

(72) Inventor: Thomas Brown, Lake Quivira, KS (US)

(73) Assignee: Brown Innovation, LLC, Lake Quivira, KS (US)

( * ) Notice: Subject to any disclaimer, the term of this patent is extended or adjusted under 35 U.S.C. 154(b) by 740 days.

(21) Appl. No.: 15/226,393

(22) Filed: Aug. 2, 2016

(65) Prior Publication Data
US 2018/0036176 A1 Feb. 8, 2018

(51) Int. Cl.
| | |
|---|---|
| *A61F 11/10* | (2006.01) |
| *B29C 44/04* | (2006.01) |
| *B29K 9/06* | (2006.01) |
| *B29K 105/04* | (2006.01) |
| *B29C 44/58* | (2006.01) |
| *B29K 101/12* | (2006.01) |
| *B29L 9/00* | (2006.01) |

(52) U.S. Cl.
CPC .......... *A61F 11/10* (2013.01); *B29C 44/0407* (2013.01); *A61F 2240/001* (2013.01); *B29C 44/588* (2013.01); *B29K 2009/06* (2013.01); *B29K 2023/06* (2013.01); *B29K 2101/12* (2013.01); *B29K 2105/043* (2013.01); *B29K 2105/045* (2013.01); *B29K 2105/046* (2013.01); *B29K 2995/007* (2013.01); *B29K 2995/0097* (2013.01); *B29L 2009/00* (2013.01)

(58) Field of Classification Search
CPC .......... A61F 11/06; A61F 11/08; A61F 11/10; A61F 11/12; A61F 2011/085; H04R 1/1016; H04R 25/652
See application file for complete search history.

(56) References Cited

U.S. PATENT DOCUMENTS

| | | | | |
|---|---|---|---|---|
| 4,461,290 | A * | 7/1984 | Gardner, Jr. | A61F 11/12 128/866 |
| 5,506,310 | A * | 4/1996 | Vasselin | A63C 5/12 525/420 |
| 5,573,015 | A * | 11/1996 | Williams | A61F 11/08 128/864 |
| 8,820,470 | B2 | 9/2014 | Brown | |

(Continued)

*Primary Examiner* — Kari K Rodriquez
(74) *Attorney, Agent, or Firm* — Hovey Williams LLP

(57) ABSTRACT

A thermoplastic elastomer (TPE) foam having a soft open-cell inner layer and a washable closed-cell outer layer which surrounds and substantially seals the inner layer, and which may be used alone or in combination with other components to produce useful articles. The TPE foam includes a base resin which is a styrenic block copolymer, and a foaming agent. A process of forming and molding the TPE foam includes using a shutoff nozzle to prevent the foaming agent from activating before reaching the mold cavity, using an oversized gate to minimize shear heat, and using oversized vents. An earplug may be constructed by molding the TPE foam over a core or body formed from a material which is denser than the TPE foam. A first earplug design may employ a constrained layer damping effect, while a second earplug design may employ an adjustable sound attenuation effect.

20 Claims, 5 Drawing Sheets

(56) References Cited

U.S. PATENT DOCUMENTS 9,278,031 B2    3/2016  Brown
2010/0307861 A1* 12/2010 Tiemens ................ C08J 9/0061
                                                  181/135

* cited by examiner

WASHABLE THERMOPLASTIC ELASTOMER FOAM AND ARTICLES INCORPORATING SAME

FIELD

The present invention relates to foams and articles incorporating foams, and more particularly to a thermoplastic elastomer foam having an open-cell inner layer and a washable closed-cell outer layer which surrounds and substantially seals the open-cell inner layer, and articles incorporating the washable thermoplastic elastomer foam.

BACKGROUND

So-called "foam earplugs" are often used to attenuate sound. Foam earplugs are typically constructed of either polyvinyl chloride (PVC) or polyurethane (PU) (so-called "memory foam") material which can be compressed and positioned in the user's ear where it expands to fill the ear. Foam earplugs suffer from several disadvantages. In particular, the open-cell structure accumulates dirt and cannot be effectively washed. The open cell structure also accumulates ear wax and oil and can harbor bacteria. As a result, foam earplugs are generally only worn once and then discarded. Further, producing and using products constructed of PVC and PU materials can involve exposure to highly toxic chemicals which can be hazardous to people and the environment. For example, PVC is made from petroleum and may include phthalates, and the production process uses sodium chloride, and PU may include isocyanates, amine catalysts, polyols, and flame retardants.

This background discussion is intended to provide information related to the present invention which is not necessarily prior art.

SUMMARY

Embodiments of the present invention solve the above-described and other problems and limitations by providing a thermoplastic elastomer (TPE) foam having a soft open-cell inner layer and a washable closed-cell outer layer which surrounds and substantially seals the open-cell inner layer, and which may be used alone or in combination with other components to produce useful articles, such as earplugs. In contrast to prior art foams, the TPE foam is less toxic to produce and articles incorporating the TPE foam can be washed and reused.

In a first embodiment, a TPE foam body may comprise an open-cell inner layer and a closed-cell outer layer. The inner and outer layers may be formed from an identical base resin which includes a styrenic block copolymer. The closed-cell outer layer may surround and substantially seal the open-cell inner layer.

Various implementations of the first embodiment may include any one or more of the following additional features. The TPE foam may have a Shore hardness value of approximately between OO 15 and OO 40. The closed-cell outer layer may be approximately between 0.015 inches and 0.020 inches thick. The TPE body may be molded in the form of an earplug adapted to be inserted and retained in an ear of a user.

In a second embodiment, an article may comprise a core and a TPE foam. The core may be constructed of a core material and include a central body having a longitudinal axis. The TPE foam may be molded over at least a portion of the core and have an open-cell inner layer and a closed-cell outer layer. The inner and outer layers may be formed from an identical base resin which includes a styrenic block copolymer. The closed-cell outer layer may surround and substantially seal the open-cell inner layer. The core material may have a higher density than the TPE foam.

Various implementations of the second embodiment may include any one or more of the following additional features. The core material may be constructed of a mixture containing a base substrate and one or more minerals of approximately between 30% and 40% total weight. The central body may have a Shore hardness value of at least A 40-80. An end of the central body may include a button structure configured to aid insertion of the article into a cavity, such as an ear of a user. The TPE foam may have a Shore hardness value of approximately between OO 15 and OO 40. The closed-cell outer layer may be approximately between 0.015 inches and 0.020 inches thick. The core may further include one or more fins arranged in a longitudinally spaced apart relationship along at least a portion of the central body and extending radially outward from the longitudinal axis of the central body. The fin structures may each have a thickness of approximately between 0.012 inches and 0.024 inches.

In a third embodiment, an article may comprise a body, a valve assembly, and a TPE foam material. The body may be constructed from a body material and include a longitudinal tunnel arranged along a longitudinal axis. The valve assembly may be constructed of a valve assembly material and coupled with the body, and include a disk defining at least one shield and at least one hole, and a knob defining at least one inlet. The knob may be repositionable relative to the disk so as to increase an alignment of the inlet with the shield and thereby decrease an amount of sound entering the longitudinal tunnel, and to increase an alignment of the inlet with the hole and thereby increase the amount of sound entering the longitudinal tunnel. The TPE foam may be molded over at least a portion of the body and have an open-cell inner layer and a closed-cell outer layer. The inner and outer layers may be formed from an identical base resin which includes a styrenic block copolymer. The closed-cell outer layer may surround and substantially seal the open-cell inner layer. The body material may have a higher density than the TPE foam.

Various implementations of the third embodiment may include any one or more of the following additional features. The body material may be constructed of a mixture containing a base substrate and one or more minerals of approximately between 30% and 40% total weight. The body may have a Shore hardness value of at least A 40-80. The valve assembly material may be harder than the body material. The knob may further include a head to facilitate grasping and repositioning the knob relative to the disk. The TPE foam may have a Shore hardness value of approximately between OO 15 and OO 40. The closed-cell outer layer may be approximately between 0.015 inches and 0.020 inches thick. The TPE material may be further molded, inserted, or otherwise provided between the disk and the knob so as to increase a seal between the disk and the knob, and/or the TPE material may be further molded, inserted, or otherwise provided between the disk and the body so as to increase a seal between the disk and the body.

In a fourth embodiment, a method of forming a TPE foam body by injection molding of a TPE base resin into a vented mold cavity may comprise the following. The TPE base resin may be mixed with a foaming agent to create a mixture. The TPE base resin may include a styrenic block copolymer having a processing profile, and the foaming agent may be approximately between 1% and 4% by total weight and may have an activation temperature that is compatible with the processing profile of the base resin. The mixture may be maintained at approximately between 240 degrees F. and 320 degrees F. A shutoff nozzle may be used to create a backpressure within the mixture of approximately between 1000 psi and 3000 psi so as to prevent the foaming agent from activating before injection into the mold cavity. At least one gate may be used which is oversized in order to minimize a shear heat at an injection speed at which the mixture is injected through the gate. The mold cavity may be heated to approximately between 100 degrees F. and 140 degrees F. to form the closed-cell outer layer having a thickness of approximately between 0.015 inches and 0.020 inches. The vented mold cavity having at least one vent that is sized to rapidly vent the mold cavity and to facilitate unconstrained foam cell growth within the mold cavity thereby forming the thermoplastic elastomer foam body comprising an open-cell inner layer and a closed-cell outer layer which surrounds and substantially seals the open-cell inner layer.

Various implementations of the fourth embodiment may include any one or more of the following additional features. The TPE foam body may have a Shore hardness value of approximately between OO 15 and OO 40. The method may further include mixing a nucleating agent into the mixture, and the nucleating agent may be talc or gypsum. The method may further include using an injection accumulator cylinder to increase the injection speed of the mixture through the at least one gate.

This summary is not intended to identify essential features of the present invention, and is not intended to be used to limit the scope of the claims. These and other aspects of the present invention are described below in greater detail.

DRAWINGS

Embodiments of the present invention are described in detail below with reference to the attached drawing figures, wherein.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment", "an embodiment", or "embodiments" mean that the feature or features referred to are included in at least one embodiment of the invention. Separate references to "one embodiment", "an embodiment", or "embodiments" in this description do not necessarily refer to the same embodiment and are not mutually exclusive unless so stated. Specifically, a feature, structure, act, etc. described in one embodiment may also be included in other embodiments, but is not necessarily included. Thus, particular implementations of the present invention can include a variety of combinations and/or integrations of the embodiments described herein.

Figure 1:
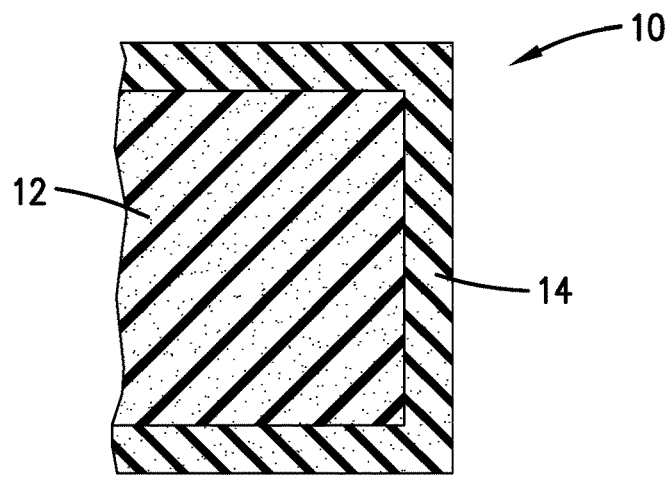
FIG. 1 is a fragmentary cross-sectional view of an embodiment of a TPE foam of the present invention.

Broadly characterized, referring to FIG. 1, embodiments of the present invention provide a thermoplastic elastomer (TPE) foam 10 having a soft open-cell inner layer 12 and a washable closed-cell outer layer 14 which surrounds and substantially seals the open-cell inner layer 12 at least from an external environment. More specifically, during formation of the TPE foam 10 in a vented mold cavity, the closed-cell outer layer 14 forms over the open-cell inner layer 12 to surround and substantially seal the open-cell inner layer 12 so that dirt or other undesirable material does not reach or accumulate in or on the open-cell inner layer 12 and can be effectively washed off of the closed-cell outer layer 14. As used herein, the phrase "substantially seals" may mean making impervious to the passage of water and/or dirt or other undesirable material or making resistant to the passage of water and/or dirt or other undesirable material. The TPE foam 10 may be used alone or in combination with other components to produce useful articles, such as earplugs. In contrast to prior art foams, the TPE foam 10 is less toxic to produce and articles incorporating the TPE foam 10 can be washed and reused.

Embodiments of the TPE foam 10 may be formed from a composition broadly comprising a base resin and a foaming agent. The base resin may be substantially any suitable styrenic block copolymer having a processing profile including a processing temperature. For at least some applications (e.g., earplugs), it may be desirable that the TPE material have a Shore hardness value of approximately between OO 15 and OO 40, and high elastomeric and flexural modulus properties. For at least some applications involving contact with skin, a TPE material approved by the U.S. Food and Drug Administration may be appropriate. Exemplary styrenic block copolymer TPE materials include styrene-butadiene-styrene (SBS) block copolymers, styrene-isoprene-styrene (SIS) block copolymers, and hydrogenated styrenic block copolymers (HSBC).

For at least some applications in which the TPE foam 10 is to be overmolded onto a substrate (examples of which are described below), it may be desirable that the base resins of both the TPE foam 10 and the substrate be molecularly compatible in order to chemically bond and adhere to each other when the TPE foam 10 is injected into the mold cavity at a desired processing temperature. In particular, if the required TPE foam injection temperature is too hot for adhesion with the substrate, then activation of the TPE foam 10 may be extreme and inconsistent, and blisters and large bubbles may occur. Low glass transition and melt temperatures for both the TPE foam 10 and the substrate may be desirable to allow for more controlled gassing and endothermic reaction prior to filling the mold cavity. The temperature profile may be a bell curve.

The foaming agent may be substantially any suitable foaming agent, such as Actifoam®, Foamisol, or Fafoam.

The foaming agent functions to reduce resin volume by releasing a gas which creates air voids in the base resin, thereby lowering overall material costs. The foaming gases may be created by endothermic decomposition. Maximum gas yields may be achieved when processing temperatures of approximately between 374 degrees F. and 437 degrees F. are reached. For some applications, the foaming agent may be provided in a powder media form in order to facilitate mixing with the base resin and achieving a mixed homogenous ratio blend. To achieve proper ratios, an amount of foaming agent of approximately between 1% and 4% total weight may be used. The activation temperature of the foaming agent should be compatible with the processing profile of the base resin.

For at least some applications, it may be desirable to add a nucleating agent, such as talc or gypsum, to create a more consistent and homogenous foam body throughout the article.

For at least some articles (e.g., earplugs) into which the TPE foam 10 may be incorporated, the washable closed-cell outer layer 14, or "skin", may be approximately between 0.015 inches and 0.020 inches thick. As discussed below in more detail, an elevated mold temperature may be used to achieve a desired thickness.

Figure 2:
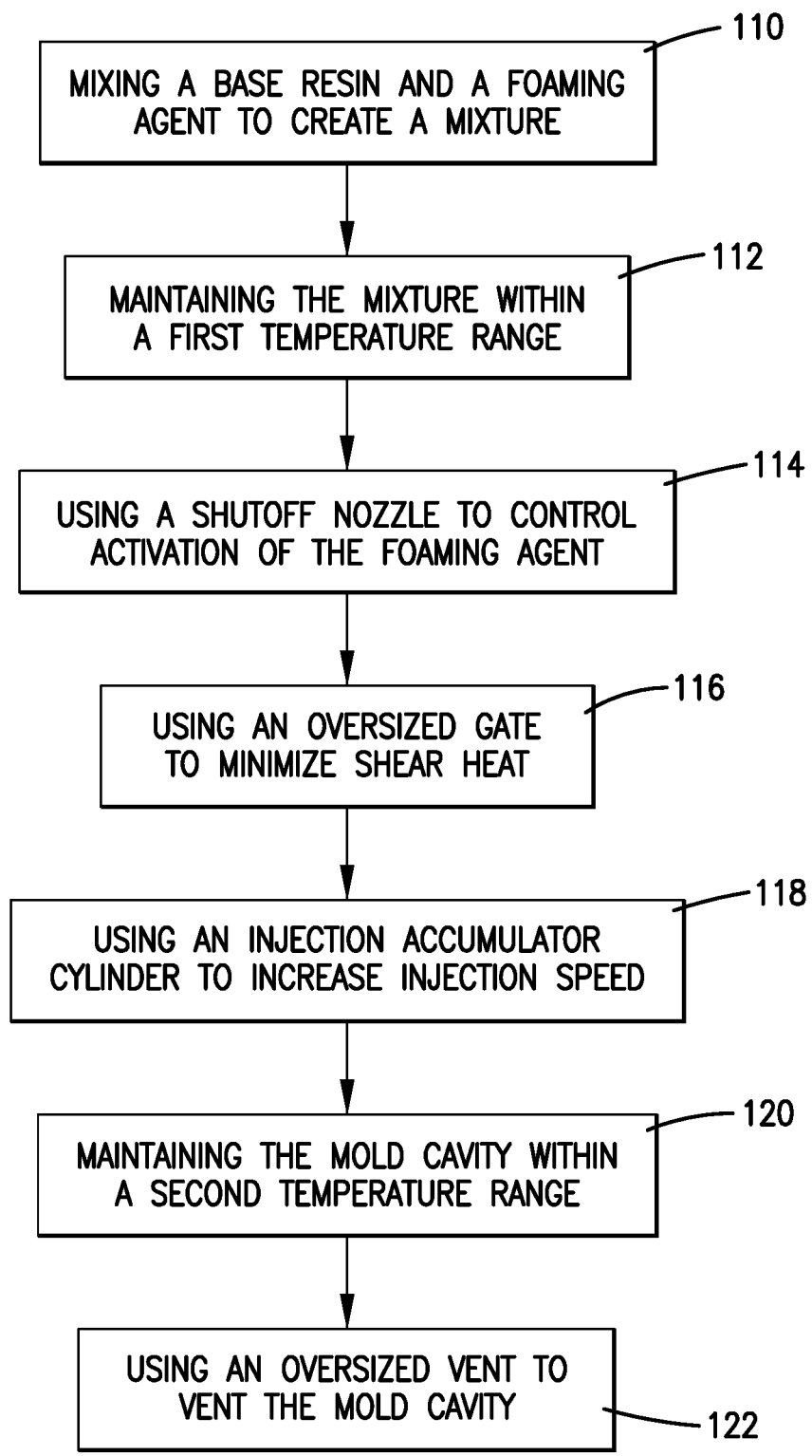
FIG. 2 is a flowchart of an embodiment of a process of forming and molding the TPE foam of FIG. 1.

Broadly characterized, referring to FIG. 2, an embodiment of a process of making and molding the TPE foam 10 may proceed substantially as follows. The base resin, foaming agent, and any other components of the composition (e.g., a nucleating agent) may be mixed, as shown in 110, to form a substantially homogenous mixture in order to create consistent and cohesive dispersement of the foam body and walls.

A temperature profile in the form of a bell curve approximately between 240 degrees F. and 320 degrees F. may be maintained, as shown in 112, in order to control the desired foaming action. Processing temperatures that are too high may create blisters, and uncontrolled endothermic reactions may create undesirable conditions within the processing equipment.

The injection unit (not shown) operable to introduce the resin mixture into the mold may be equipped with a shutoff nozzle operable to deliver approximately between 1000 psi and 3000 psi of back pressure into the injection unit barrel, as shown in 114, to prevent foam cell formation in the system before the mixture reaches the mold cavity. Pressure drops prior to cavity fill may be minimized, and significant drops upon reaching the cavity, spurs, and/or runners may be kept short and sealed off. After the injection cycle, no packing may be required with an unconstrained cavity fill.

At least one gate may be used which is approximately between two to four times the gate size that might normally be used for this type of injection molding process, as shown in 116, in order to minimize shear heat at high injection speed. Further, an injection accumulator cylinder may be used, as shown in 118, to increase injection speed through the gate and reduce the time before the pressure drops.

To create the washable closed-cell outer layer 14, the mold cavity may be heated to approximately between 100 degrees F. and 140 degrees F., as shown in 120, depending on such factors as the foaming agent, the mold material, and the cavity volume and shape. Higher cavity temperatures may result in a thicker outer layer 14, so the cavity temperature may be chosen to balance the thickness of the outer layer 14 with the thickness of the inner layer 12 to achieve a desired overall result.

At least one vent may be used which is approximately between fifteen and twenty times the vent size which might normally be used for this type of injection molding process, as shown in 122, in order to minimize constraint and inhibition on endothermic cell formation and thereby facilitate fully populating the mold cavity with the TPE foam material. Larger vents may allow the TPE foam material to enter the vents, and so it may be desirable to trim any excess material from the finished article.

Figure 3:
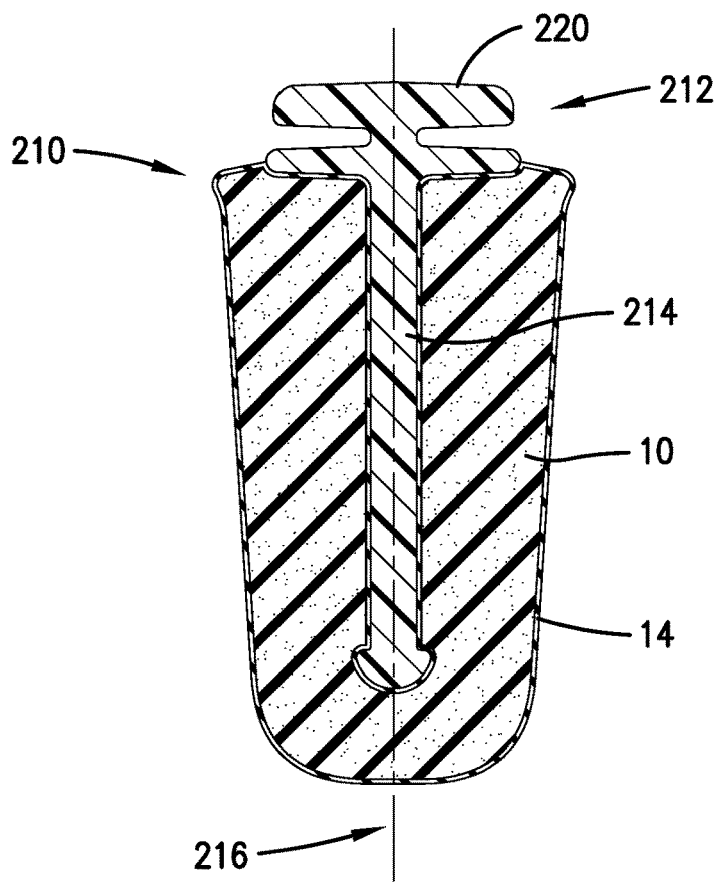
FIG. 3 is a cross-sectional elevation view of a first embodiment of a constrained layer damping earplug article constructed using the TPE foam of FIG. 1.

The TPE foam 10 having a washable closed-cell outer layer 14 may be employed alone or in combination with other components to create useful articles. Broadly characterized, referring to FIGS. 3 and 4, one such useful article may be an earplug 210 providing a constrained layer damping effect. An embodiment of the earplug 210 may broadly include a sound damping core component 212 over at least a portion of which the TPE foam 10 may be molded. The core component 212 may include a central body 214 having a longitudinal axis 216, and may further include one or more fin structures 218 (seen in FIG. 4) arranged in a spaced apart relation along at least a portion of the central body 214 and extending radially (e.g., substantially perpendicularly) outward from the longitudinal axis 216 of the central body 214.

The sound damping core material should be compatible with the TPE foam material to facilitate the overmolding process. The core material may be formed of a mixture including a base substrate and a sound damping filler. Substantially any suitable sound damping filler may be used, such as one or more minerals of approximately between 30% and 50% total weight and blended substantially homogenously with the base substrate.

For at least some applications, the core material may have a Shore hardness value of approximately A 40-80 in order to facilitate proper insertion and comfort. In particular, the dense but flexible core may act as a plunger for the earplug fitting process by providing sufficient rigidity to push the end covered by the TPE foam 10 into the ear. Relatedly, the opposite end of the central body 214 may present a button or other structure 220 to further facilitate pushing the earplug into the ear.

Figure 4:
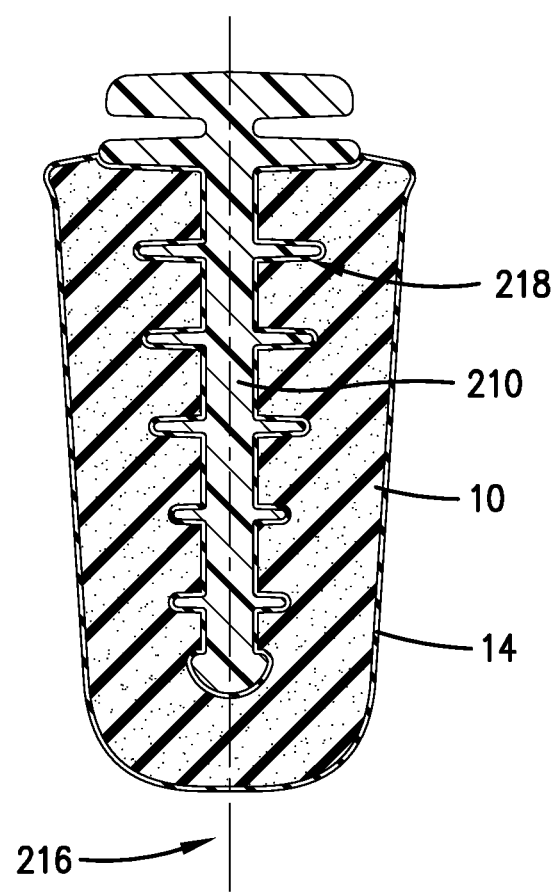
FIG. 4 is a cross-sectional elevation view of a second embodiment of the constrained layer damping earplug article constructed using the TPE foam of FIG. 1.
Figure 5:
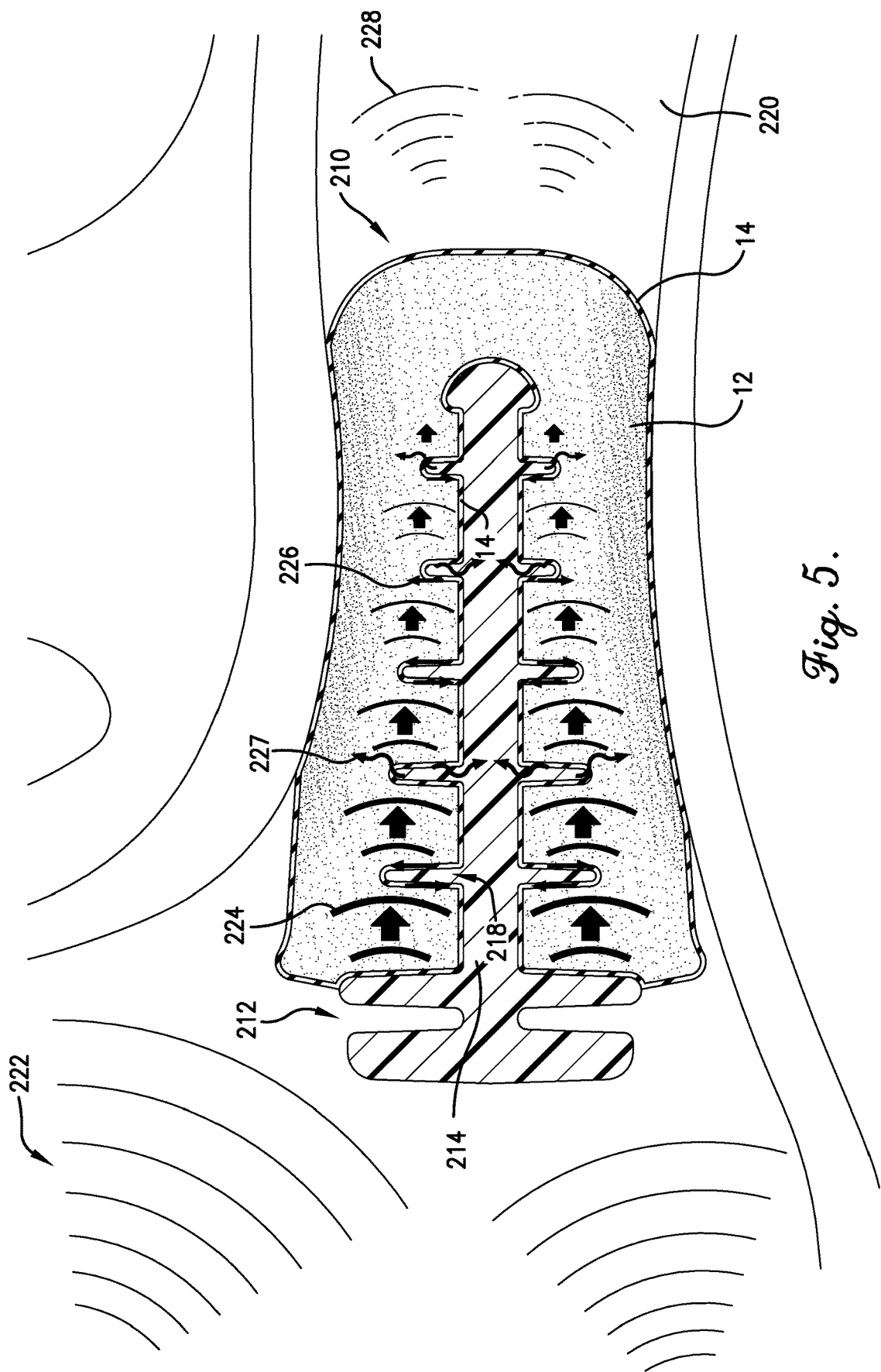
FIG. 5 is a fragmentary cross-sectional elevation view of the earplug article of FIG. 4.

The core material may have a higher density than the TPE foam 10 so that once the TPE foam 10 is molded over at least a portion of the core component 212 that is insertable into the ear canal 220 (FIG. 5), the different layers of materials having different densities may function to dampen sound entering the ear. More specifically, the higher density minerals or fillers and lower density inner and outer layers may function to modify the path of sound propagation. As a result, the constrained damping design may dissipate and reduce the amplitude of sound waves through noise reflection (reflecting the sound waves off one or more barriers), noise absorption (converting acoustic energy into heat energy), and noise dissipation (distorting the sound waves through multiple layers). Referring to FIGS. 4 and 5, this effect may be significantly enhanced by the addition of the one or more fins structures 218 so that sound waves encounter multiple layers of the materials having different densities. For at least some applications, the fin structures 218 may be approximately between 0.012 inches and 0.024 inches in thickness. If the fin structures are too thin, they may not provide a desired level of constrained layer damping, and if the fin structures are too thick, they may interfere with fit and comfort. As shown in FIG. 5, in particular, the closed cell layer 14 also forms on the interface between the open cell layer 12 and central body 214. Thus, sound waves traversing the central axial portion of the ear plug are directed through numerous transitions between materials of different density. For example, the sound wave may initially pass through closed cell layer 14 into open cell layer 12, through closed cell layer 14, through fin structure 218, through closed cell layer 14, through open cell layer 12, etc. As depicted in FIG. 5, soundwaves 222 impinging upon the ear canal 220 are directed through ear plug 210. At least a portion of the soundwaves 224 that pass through portions of ear plug 210 are deflected in response to passage through the varying components of differing density that comprise the ear plug. This change in direction, indicated by arrows 226, results in sound being directed away from the interior portion of ear canal 220, and thus away from the user's ear drum (not shown). In addition, at least a portion of the sound energy traveling through the various layers of differing density are dissipated as heat, represented by arrows 227. The constrained layer damping effect produced by ear plug 210 results in the transmission of soundwaves 228 into the interior of ear canal 220 that are greatly reduced in intensity as compared to soundwaves 222.

Figure 6:
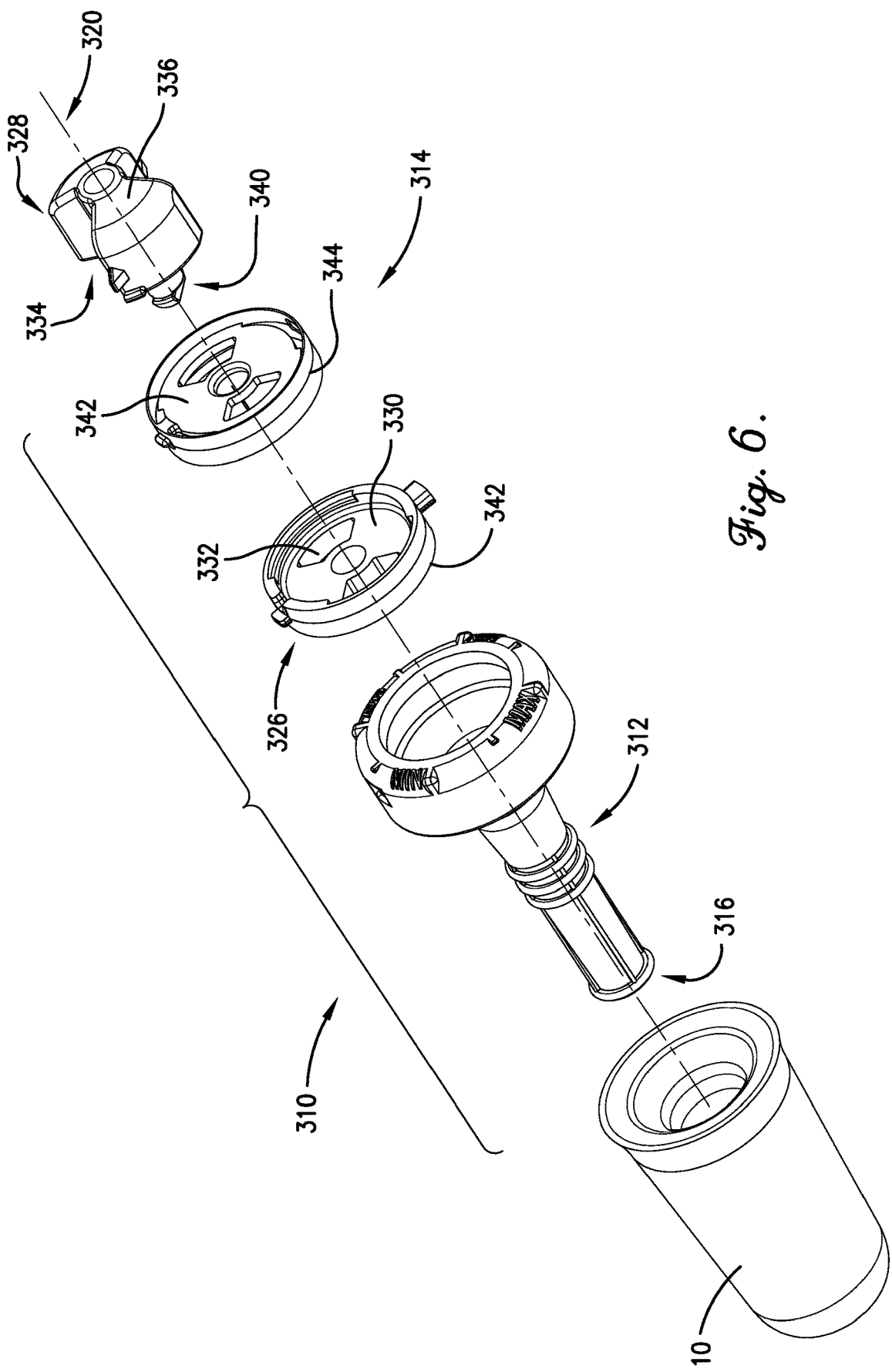
FIG. 6 is an exploded isometric view of an embodiment of a sound attenuation earplug article constructed using the TPE foam of FIG. 1.

Broadly characterized, referring to FIG. 6, another such useful article may be an earplug 310 providing an adjustable sound attenuation effect. Details of an exemplary sound attenuating earplug may be found in U.S. Pat. Nos. 8,820,470 and 9,278,031, the contents of both of which are hereby incorporated by reference into the present discussion in their entireties. An embodiment of the earplug 310 may broadly include a body 312 and a valve assembly 314 over at least a portion of which the TPE foam 10 may be molded or otherwise applied.

The body 312 may have a generally elongated shape and define a longitudinal tunnel 316 arranged along a longitudinal axis 320. The body 312 may be constructed of substantially any suitable material, such as a polymer material having a relatively soft Shore hardness value, such as, for example, ASTM D2240 type A polypropylene, or the same or similar material as the earplug 210, described above, having a Shore hardness value of approximately A 40-80 in order to facilitate proper insertion and comfort.

The valve assembly 314 may include a mated disk 326 and knob 328. The knob 328 may be rotatable, slidable, or otherwise repositionable relative to the disk 326 in order to adjustably attenuate sound. In one implementation, the knob 328 may include a split prong 340, and the disk 326 may present a through-hole 342, and the knob 328 may be rotatably coupled with the disk 326 by the split prong 340 extending through and engaging the through-hole 342. The valve assembly 314 may be constructed of a harder material than the body 312 so as to transfer the applied forces and accomplish overall function of the earplug 310. As such, the valve assembly 314 may be constructed of cellulose, metal, or polymers such as polypropylene, polyurethane, polyethylene, or blends thereof. The valve assembly 314 may be removably coupled to the body 312, so as to facilitate cleaning and maintenance of the ear plug 310.

The disk 326 may alternately define at least one shield 330 and at least one hole 332, and more preferably, a plurality of shields 330 and holes 332. The knob 328 may define at least one inlet 334, and more preferably, first and second inlets 334, and may include a head 336 configured to facilitate grasping and manipulating the knob 328. The inlets 334 of the knob 328 operate in conjunction with the shields 330 and the holes 332 of the disk 326, such that rotating the knob 328 to increase the alignment of the inlets 334 and the shields 330 decreases the amount of sound entering the tunnel 316, and rotating the knob to increase the alignment of the inlets 334 and the holes 332 increases the amount of sound entering the tunnel 316. Thus, in operation, a user wearing the earplug 310 may manually rotate the head 336 of the knob 328, so as to gradually align the inlets 334 with the shields 330 or the holes 332 in order to respectively increase or decrease the sound attenuation effect.

The TPE foam 10 may be incorporated into the earplug 310 in at least either or both of two ways. First, the TPE foam 10 may be molded over at least a portion of the body 312 that is insertable into the ear. Second, the TPE foam 10 may be molded, applied, or otherwise positioned as a gasket or membrane 342 between the knob 328 and the disk 326 and/or as a gasket or membrane 344 between the disk 326 and the body 312 in order to enhance the pneumatic and acoustic seals therebetween. In some applications, the seal may be configured to slowly leak so as to equalize a pressure difference between the interior of the longitudinal tunnel 316 and the external environment, which may be advantageous in certain contexts, such as when traveling in an airplane.

In certain embodiments described herein, the ear plugs are capable of achieving a noise reduction rating (NRR) of at least 30 dB, at least 33 dB, or at least 34 dB.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. An earplug adapted to be inserted and retained in an ear of a user comprising:
   a core constructed of a core material and including a central body having a longitudinal axis and a pair of spaced apart ends, the central body comprising two or more fins arranged in a longitudinally spaced apart relationship along at least a portion of the central body and inwardly spaced from the pair of spaced apart ends, the two or more fins extending radially outward from the longitudinal axis of the central body and comprising opposed proximal and distal surfaces;
   a thermoplastic elastomer foam body injection molded over at least a portion of the core, and comprising an open-cell inner layer and a closed-cell outer layer, both the open-cell inner layer and the closed-cell outer layer being formed from a base resin which includes a styrenic block copolymer, the foam body directly contacting both the proximal and distal fin surfaces,
   the earplug comprising
      a proximal end and an opposed distal end that is configured to be inserted into an ear canal of the user, and
      the closed-cell outer layer surrounding and sealing the open-cell inner layer at the distal end of the foam body,
   wherein the core material has a higher density than the thermoplastic elastomer foam.

2. The thermoplastic elastomer foam body of claim 1, wherein the thermoplastic elastomer foam body has a Shore hardness value of between OO 15 and OO 40.

3. The thermoplastic elastomer foam body of claim 1, wherein the closed-cell outer layer is between 0.015 inches and 0.020 inches thick.

4. An earplug adapted to be inserted and retained in an ear of a user comprising:
   a core constructed of a core material and including a central body having a longitudinal axis; and
   a thermoplastic elastomer foam injection molded over at least a portion of the core and having an open-cell inner layer and a closed-cell outer layer, both the open-cell inner layer and the closed-cell outer layer being formed from a base resin which includes a styrenic block copolymer, the earplug comprising a proximal end defined by a proximal end margin and an opposed distal end defined by a distal end margin, the distal end configured to be inserted into an ear canal of the user, the closed-cell outer layer surrounding and sealing the open-cell inner layer at the distal end of the earplug, wherein the core material has a higher density than the thermoplastic elastomer foam, wherein an end of the core at the proximal end of the earplug includes a button structure extending outwardly beyond the proximal end margin of the earplug proximal end, the button structure comprising a first relatively flat element having a distal surface that is in contact with the thermoplastic elastomer foam and a proximal surface that is spaced apart from the thermoplastic elastomer foam, and a second relatively flat element having distal and proximal surfaces that are spaced apart from the thermoplastic elastomer foam, the distal surface of the second element being spaced from the proximal surface of the first element, the first and second elements being interconnected by a neck structure that is unitary with the core, the button structure being configured to aid insertion and removal of the ear plug from the user's ear canal.

5. The article of claim 4, wherein the core material is constructed of a mixture containing a base substrate and one or more minerals of between 30% and 40% total weight.

6. The article of claim 4, wherein the central body has a Shore hardness value of at least A 40-80.

7. The article of claim 4, wherein the thermoplastic elastomer foam has a Shore hardness value of between OO 15 and OO 40.

8. The article of claim 4, wherein the closed-cell outer layer is between 0.015 inches and 0.020 inches thick.

9. The article of claim 4, the core further including two or more fins arranged in a longitudinally spaced apart relationship along at least a portion of the central body and extending radially outward from the longitudinal axis of the central body.

10. The article of claim 9, wherein the one or more fin structures each have a thickness of between 0.012 inches and 0.024 inches.

11. A method of forming an earplug comprising a thermoplastic elastomer foam body over a core, the earplug having a proximal end defined by a proximal end margin and an opposed distal end defined by a distal end margin configured to be inserted into an ear canal of the user, the earplug formed by injection molding of a thermoplastic elastomer base resin into a vented mold cavity, the method comprising the steps of:

positioning the core within the mold cavity, the core constructed of a core material having a higher density than the thermoplastic elastomer base resin, and including a central body having a longitudinal axis and a button structure located at the proximal end so as to extend outwardly beyond the proximal end margin of the earplug proximal end, the button structure comprising a first relatively flat element having a distal surface that is in contact with the thermoplastic elastomer foam body and a proximal surface that is spaced apart from the thermoplastic elastomer foam, and a second relatively flat element having distal and proximal surfaces that are spaced apart from the thermoplastic elastomer foam body, the distal surface of the second element being spaced from the proximal surface of the first element, the first and second elements being interconnected by a neck structure that is unitary with the core, the button structure being configured to aid insertion and removal of the earplug from the user's ear canal;

mixing the thermoplastic elastomer base resin and a foaming agent to create a mixture, wherein the base resin includes a styrenic block copolymer having a processing profile, the foaming agent is between 1% and 4% by total weight, and the foaming agent having an activation temperature which is compatible with the processing profile of the base resin;

maintaining the mixture at between 240 degrees F. and 320 degrees F.;

using a shutoff nozzle to create a backpressure within the mixture of between 1000 psi and 3000 psi so as to prevent the foaming agent from activating before injection into the mold cavity;

using at least one gate which is oversized in order to minimize a shear heat at an injection speed at which the mixture is injected through the at least one gate; and heating the mold cavity to between 100 degrees F. and 140 degrees F. to form the closed-cell outer layer having a thickness of between 0.015 inches and 0.020 inches; the vented mold cavity having at least one vent that is sized to rapidly vent the mold cavity and to facilitate unconstrained foam cell growth within the mold cavity thereby forming the thermoplastic elastomer foam body comprising an open-cell inner layer and a closed-cell outer layer which surrounds and seals the open-cell inner layer at the distal end of the foam body.

12. The method of claim 11, wherein the thermoplastic elastomer foam body has a Shore hardness value of between OO 15 and OO 40.

13. The method of claim 11, further including mixing a nucleating agent into the mixture.

14. The method of claim 13, wherein the nucleating agent is talc or gypsum.

15. The method of claim 11, further including using an injection accumulator cylinder to increase the injection speed of the mixture through the at least one gate.

16. A method of forming an earplug comprising a thermoplastic elastomer foam body over a core, the earplug having a proximal end and an opposed distal end that is configured to be inserted into an ear canal of the user, the earplug formed by injection molding of a thermoplastic elastomer base resin into a vented mold cavity, the method comprising the steps of:

positioning the core within the mold cavity, the core constructed of a core material having a higher density than the thermoplastic elastomer base resin, and including a central body having a longitudinal axis and a pair of spaced apart ends, the central body including two or more fins arranged in a longitudinally spaced apart relationship along at least a portion of the central body and inwardly spaced from the pair of spaced apart ends, the two or more fins extending radially outward from the longitudinal axis of the central body and comprising opposed proximal and distal surfaces;

mixing the thermoplastic elastomer base resin and a foaming agent to create a mixture, wherein the base resin includes a styrenic block copolymer having a processing profile, the foaming agent is between 1% and 4% by total weight, and the foaming agent having an activation temperature which is compatible with the processing profile of the base resin;

maintaining the mixture at between 240 degrees F. and 320 degrees F.;

using a shutoff nozzle to create a backpressure within the mixture of between 1000 psi and 3000 psi so as to prevent the foaming agent from activating before injection into the mold cavity;

using at least one gate which is oversized in order to minimize a shear heat at an injection speed at which the mixture is injected through the at least one gate; and heating the mold cavity to between 100 degrees F. and 140 degrees F. to form the closed-cell outer layer having a thickness of between 0.015 inches and 0.020 inches; the vented mold cavity having at least one vent that is sized to rapidly vent the mold cavity and to facilitate unconstrained foam cell growth within the mold cavity thereby forming the thermoplastic elastomer foam body comprising an open-cell inner layer and a closed-cell outer layer which surrounds and seals the open-cell inner layer at the distal end of the foam body, the foam body directly contacting and enveloping both the proximal and distal fin surfaces.

17. The method of claim 16, wherein the thermoplastic elastomer foam body has a Shore hardness value of between OO 15 and OO 40.

18. The method of claim 16, further including mixing a nucleating agent into the mixture.

19. The method of claim 18, wherein the nucleating agent is talc or gypsum.

20. The method of claim 16, further including using an injection accumulator cylinder to increase the injection speed of the mixture through the at least one gate.

* * * * *